… [11] Patent Number: 4,975,051
… [45] Date of Patent: Dec. 4, 1990

United States Patent [19]
Kargas et al.

[54] INSTRUMENT FOR ATTACHING AND REMOVING ORTHODONTIC ELASTIC BANDS

[75] Inventors: George A. Kargas; Steve E. A. Kargas, both of Madison, Wis.

[73] Assignee: Ordontics, Inc., Madison, Wis.

[21] Appl. No.: 337,263

[22] Filed: Apr. 13, 1989

[51] Int. Cl.⁵ .............................................. A61C 3/00
[52] U.S. Cl. ...................................................... 433/3
[58] Field of Search ............................. 433/2, 3, 141

[56] References Cited

FOREIGN PATENT DOCUMENTS 48503  3/1985  U.S.S.R. ................................. 433/3

*Primary Examiner*—Cary E. Stone
*Attorney, Agent, or Firm*—Carl E. Gulbrandsen

[57] ABSTRACT

An orthodontic instrument is described having a generally elongated handle of large diameter and non-circular cross-section, having a serrated surface, having generally thin end of circular cross-section, having a rounded fluke at the thin end, and having an oppositely disposed fluke which faces toward the large diameter end of the handle. The rounded fluke defines a relatively short and wide aperture, while the opposite fluke defines a relatively long and narrow aperture.

5 Claims, 1 Drawing Sheet

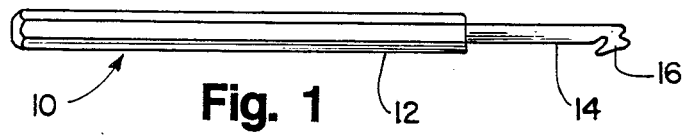
Fig. 1
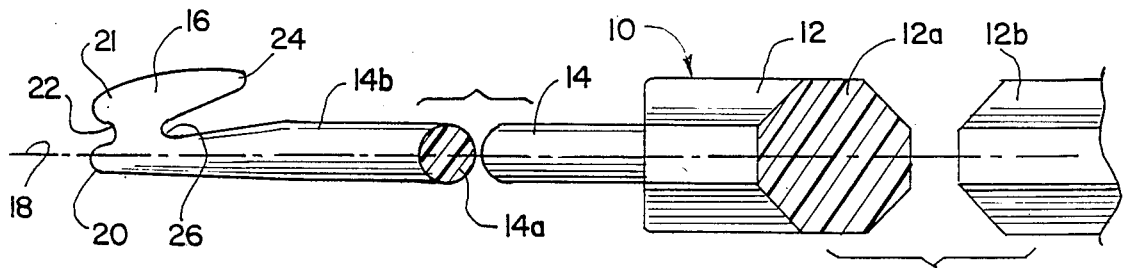
Fig. 2
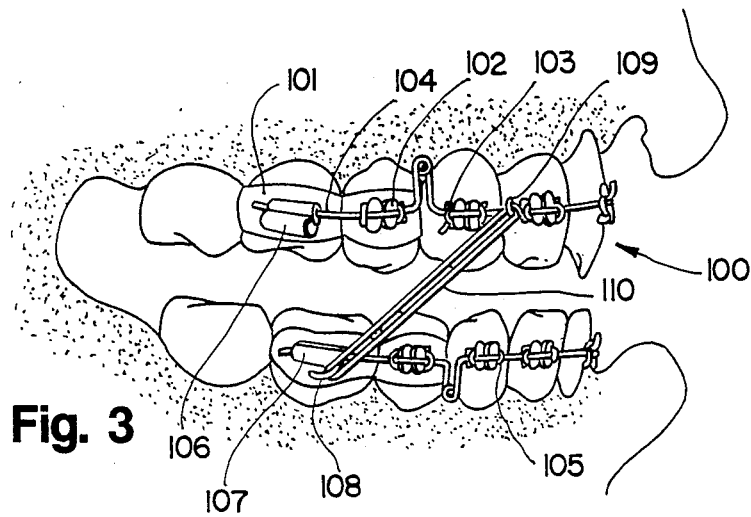
Fig. 3
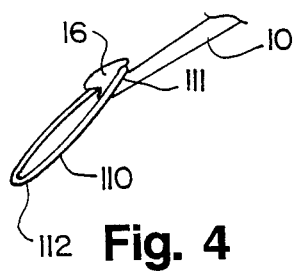
Fig. 4
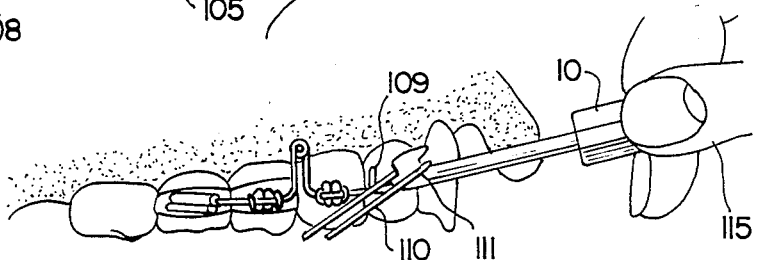
Fig. 5
Fig. 7A
Fig. 6
Fig. 7B
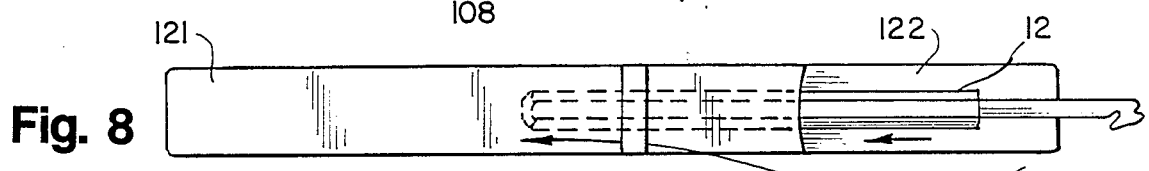
Fig. 8
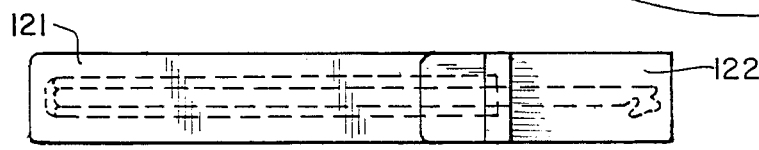
Fig. 9

INSTRUMENT FOR ATTACHING AND REMOVING ORTHODONTIC ELASTIC BANDS

TECHNICAL FIELD

This invention relates to the general subject matter of dentistry and, in particular, to the subjects of orthodontics and orthodontic appliances.

BACKGROUND OF THE INVENTION

Orthodontics is a branch of dentistry which deals with abnormalities in tooth position and jaw relationships that result in facial disharmony and malfunction. The objective of orthodontic treatment is to establish normal occlusion and facial harmony. This is achieved by repositioning the teeth and jaws often by the use of mechanical force applied with fixed or removable appliances. An orthodontic appliance is a device, either fixed to the teeth or removable, that applies force to the teeth and their supporting structures to produce changes in the relationship of the teeth to each other and to control their growth and development.

A device commonly used in the application of orthodontic appliances is an orthodontic elastic band. Such an elastic band is of great value in correction of deficiencies and in the alignment of the teeth. Such an elastic band comprises a strong flexible band which can be attached between or within upper and lower sets of orthodontic appliances so that the band exerts tension which gradually corrects the orthodontic deficiency over an extended period of time. The elastic bands are connected at each end to a hook projecting from a band carried on a tooth.

Orthodontic elastic bands are generally replaced at prescribed intervals. The replacement of such an elastic band is not an easy task and is particularly difficult when using simply the fingers of the patient or their dentist. Patients often become frustrated; consequently, elastic bands are not changed with proper frequency and it takes longer for the teeth to be repositioned.

Several devices have been proposed to help one in the insertion and removal of orthodontic elastic bands. For example, there is a device covered by U.S. Pat. No. 3,475,818. The applicator covered by the '818 patent comprises two pair of oppositely disposed lugs around which a stretched orthodontic elastic band is located to form a generally rectangular pocket. The stretched orthodontic elastic band is inserted by positioning the tooth mounted anchor hooks into the pocket and then removing the tool. Another device or tool is described in U.S. Pat. No. 4,512,739. The '739 device comprises a large U-shaped frame having cooperatively positioned, oppositely disposed grooves at its ends which are used to position the orthodontic elastic band.

Two commercial products that are used for the purpose of inserting and removing an orthodontic elastic band are known to exist. One is called an "elastic engager" and is made by the A - Company, Inc. of San Diego, California. The elastic engager tool is relatively short (approximately 2"). It comprises a short, generally flat, relatively flimsy, and inherently disposable piece of flat plastic which has a flat J-shaped hook (approximately ⅛" long) at one end. Another tool is sold by EOP Incorporated of Minneapolis, Minnesota. Their tool is sold under the Handy Hook Trademark. The handy hook tool is similar to the elastic engager tool with the exception that the handy hook tool has a short flat C-shaped projection located opposite to the J-shaped hooked end.

One major disadvantage of the handy hook tool and the elastic engager tool is that they are very short in length, such that the user of the tool often has to have the thumb and forefingers very close to if not inside the mouth. These short tools are especially difficult for adults to use. The short length and the need to place the fingers in close proximity to the mouth can be unsanitary, unsightly, and socially distasteful. What is needed is a tool for easily inserting and removing orthodontic elastic bands which can be easily grasped by an adult or a child, which can be efficiently and hygienically used, which is easily gripped, and which is inexpensive to manufacture. Such a tool will increase patient compliance, improve the application of restorative forces, and promote better oral hygiene.

Summary of the Invention

In accordance with the present invention, a tool is described for adding and removing orthodontic elastic bands on tooth anchor hooks. Specifically, the tool comprises a handle having a relatively large diameter end which has a polygonal cross-section and a serrated surface for being grasped by the thumb and fingers of the human hand, having a relatively thin and smooth opposite end which has a circular cross-section and a fitting which is flaringly and radially carried by the thin end of the handle. The fitting has two oppositely disposed horns for engaging an orthodontic elastic band. One of the horns defines with the handle an elongated generally U-shaped aperture which faces the relatively large diameter end of the handle. The other horn defines with the handle a foreshortened generally U-shaped aperture. The tool is preferably made from a durable and unbreakable plastic. The long handle facilitates use of the tool by adults and children. The relatively thin end is easily inserted into the mouth. Even side brackets can be engaged without difficulty. The short thin end allows the tool to be used with a minimum of pain and injury to the gums.

Numerous other advantages and features of the present invention will become readily apparent from the following detailed description of the invention, the embodiments described therein, from the claims, and from the accompanying drawings. Similarly, the tool may be injection molded in a variety of differently colored plastic materials.

Brief Description of the Drawings

FIG. 1 is a side view of the instrument that is the subject of the present invention;

FIG. 2 is a partial enlarged view of the fitting at the end of the instrument of FIG. 1;

FIG. 3 is a pictorial representation of the jaws of the human mouth with an orthodontic appliance attached;

FIG. 4 is a partial pictorial view of the instrument of FIG. 1 while carrying an orthodontic elastic band;

FIG. 5 is a partial pictorial view of the instrument of FIG. 1 while being used to remove an orthodontic elastic band from the upper jaw;

FIG. 6 is a partial pictorial view of the instrument of FIG. 1 while being used to remove an orthodontic elastic band from the lower jaw; and FIGS. 7A through 7B are representations of other fitting arrangements.

Detailed Description of the Preferred Embodiment

While this invention is susceptible of embodiment in many different forms, there is shown in the drawings, and will herein be described in detail, one specific embodiment of the invention. It should be understood, however, that the present disclosure is to be considered as an exemplification of the principles of the invention and is not intended to limit the invention to the specific embodiment illustrated.

Before describing the tool that is the subject of the present invention, the environment in which the invention is used will be briefly described. FIG. 3 illustrates a common orthodontic appliance 100 comprising: a band 101, a bracket 102, a tie wire 103, an arch wire 104, an elastic ligature 105, a headgear tube 106, and a buccal tube 107. An orthodontic elastic band 110 is held in tension between anchor hooks 108 and 109 on the lower and upper jaws.

Turning to FIG. 1, the orthodontic instrument or tool 10 that is the subject of the present invention is illustrated. The tool 10 comprises a generally elongated shaft or handle 12, a shaft extension 14, and an orthodontic elastic band engaging fitting 16. The elongated shaft 12 has two opposite ends. The elongated shaft 12 preferably has a polygonal cross-section 12a and a serrated surface 12b. The shaft extension 14 preferably has a circular cross-section 14a and a smooth exterior surface 14b. One end of the shaft extension 14 is joined to one end of the elongated shaft 12 and the opposite end is joined to the fitting 16. The shaft extension 14 has a diameter which is less than that of the elongated shaft 12. The thin circular cross-section of the shaft extension 14 facilitates inserting the tool 10 between the cheek and gums of the human mouth. In one embodiment, the tool 10 has an overall length of 5.25 inches (13.34 cm). Preferably the tool is formed in one piece by injection molding.

Turning now to FIG. 2, the orthodontic elastic band engaging fitting 16 will now be described in greater detail. The fitting 16 resembles a two-horned cleat. The fitting 16 is flaringly and smoothly joined to the free end of the shaft extension 14 and is located radially relative to the longitudinal axis 18 of the tool. The horn 21 at the interior or forward end 20 of the fitting forms with the shaft extension 14 a relatively foreshortened, generally C- or U-shaped aperture 22. Located at the opposite end of the fitting 16 or intermediate the ends of the shaft extension 14 is a second horn or fluke 24 which forms, with the shaft extension, a relatively elongated, generally V-shaped aperture 26. Each of the two apertures 22 and 26 is of sufficient size to fit around or engage an orthodontic elastic band. The forward aperture 22 facilitates pushing that end of an orthodontic elastic band which is located farther into the interior of the mouth. The opposite aperture 26 facilitates pulling that end of the orthodontic elastic band located closer to the front of the mouth. Preferably, the opposite aperture 26 has a throat of width sufficiently less than that of the diameter of an orthodontic elastic band, such that when an orthodontic elastic band is forced into the interior of its throat, the orthodontic elastic band is removably and grippingly held therein (See FIG. 4).

Turning to FIGS. 5 and 6, one manner in which the 10 instrument 10 may be used will be described. First, one end 111 of an orthodontic elastic band 110 is snared in the V-shaped aperture 26, thereby removably gripping the orthodontic elastic band at the interior end of the tool 10 (See FIG. 4). Next, the tool 10 is inserted into the mouth where the free end 112 of the orthodontic elastic band is lassoed on an anchor hook 108 projecting from a band or like structure attached to a tooth of the lower jaw. Afterwards, the tool 10 is withdrawn upwardly from the interior of the mouth so as to lasso the opposite end 111 of the orthodontic elastic band 110 around the anchor hook 109 carried by a tooth on the upper jaw (See FIG. 5). A slight manipulation of the tool 10 inwardly with the thumb and forefinger of the hand 115 will release the orthontic elastic band 110 from the V-shaped aperture 26. The opposite aperture 22 of the fixture 16 can then be used to adjust the orthodontic elastic band 110 between the two anchor hooks 108 and 109 (See FIG. 6).

To remove the orthodontic elastic band 110, the user can use the C-shaped aperture 22 at the interior end of the tool 10 to apply tension to the orthodontic elastic band and remove it from the lower interior anchor hook 108 (See FIG. 6) and then use the V-shaped aperture 26 to snare the orthodontic elastic band and remove it from the upper anchor hook 109. Alternatively, the tool 10 can be manipulated opposite 10 to that which was used to insert the orthodontic elastic band 110. Specifically, the V-shaped aperture 26 at the interior end of the tool 10 is used to capture the upper end 111 of the orthodontic elastic band 110 and remove it from the upper anchor hook 109 (See FIG. 5). Since the V-shaped aperture 26 will removably hold the orthodontic elastic band 110 in its throat, the tool 10 can be used to release the tension in the orthodontic elastic band and remove the opposite end 112 of the orthodontic elastic band from the lower anchor hook 108.

From the foregoing description, it will be observed that numerous variations, alternatives and modifications will be apparent to those skilled in the art. Accordingly, this description is to be construed as illustrative only and is for the purpose of teaching those skilled in the art the manner of carrying out the invention. For example, various changes may be made in the shape and arrangement of the horns forming the apertures of the orthodontic elastic band engaging fitting 16. These are shown in FIGS. 7A through 7D. In addition, equivalent elements may be substituted for those illustrated and described herein, parts may be reversed, and certain features of the invention may be utilized independently of other features of the invention. Furthermore, as illustrated in FIGS. 7 and 8, the tool may be attractively stored in a handy vinyl case 121 having tucked end-flaps 122 to provide dust proof, moisture resistant protection. Such a case provides long term protection and allows the tool to be easily stored in a purse or pocket. Thus, it will be appreciated that various modifications, alternatives, variations, etc., may be made without departing from the spirit and scope of the invention as defined in the appended claims. It is, of course, intended to cover by the appended claims all such modifications as fall within the scope of the claims.

I claim:

1. A tool for placing orthodontic elastic bands on tooth anchor hooks, comprising:
    (a) an elongated shaft which has one end which is adapted to be grasped by the human hand and which has an inside and an outside end;
    (b) a shaft extension having a free end and an opposite connected end which is joined to said inside end of said shaft, said shaft extension having a diameter which is less than that of said elongated shaft, said shaft extension having rounded, smooth surfaces and adapted to fit between the cheek and gums of a human mouth; and (c) cleat means, joined radially to said free end of said shaft extension, for engaging an orthodontic elastic band, said cleat means having two oppositely disposed smooth, rounded, horns, one of said horns defining with said shaft extension an elongated opening which faces said interior end of said shaft, and the other horn defining with said shaft extension a fore-shortened opening.

2. The tool of claim 1, wherein said fore-shortened opening of said other horn is generally U-shaped and said elongated opening of said one horn is generally V-shaped.

3. The claim of claim 2, wherein the open end of said elongated opening is of greater diameter than the cross section diameter of said elastic band and wherein said elongated opening closes to a diameter smaller than the cross sectional diameter of said elastic band such that said elastic band can be engaged in said aperture and removably and grippingly held therein.

4. The tool of claim 1, wherein said shaft extension is integrally joined to said elongated shaft and to said cleat means; and wherein said shaft extension and said elongated shaft and said cleat means are formed by injection molding.

5. A device for applying and removing orthodontic elastic bands on tooth anchor hooks, comprising:

(a) handle means having one end of large diameter relative to said opposite end, said one end adapted for being grasped by the thumb and finger of a human hand and said opposite end being relatively thin and smooth and adapted to fit between the cheek and gums of a human mouth; and (b) a fitting which is flaringly and radially carried by said thin opposite end of said handle means, said fitting having two oppositely disposed and generally rounded horns for engaging an orthodontic elastic band, one of said horns defining with said handle means an elongated generally V-shaped aperture which opens to said relatively large diameter end, the opening of said V-shaped aperture being of greater diameter than the cross sectional diameter of said elastic band, said V-shaped aperture closing to a diameter smaller than the cross sectional diameter of said elastic band such that said elastic band can be engaged in said aperture and removably and grippingly held therein, and the other horn defining with said handle means a fore-shortened generally C-shaped aperture for pushing and guiding said elastic band.

* * * * *